United States Patent [19]

Pines et al.

[11] Patent Number: 4,769,234

[45] Date of Patent: Sep. 6, 1988

[54] SKIN CARE COMPOSITIONS CONTAINING POLYVALENT EQUINE IMMUNE SERUM

[75] Inventors: Ricardo Pines, Coral Gables, Fla.; Peter M. Stephan, London, England

[73] Assignee: Peter M. Stephan Center Ltd., Miami, Fla.

[21] Appl. No.: 104,890

[22] Filed: Oct. 6, 1987

[51] Int. Cl.⁴ ........................................... A61K 39/395
[52] U.S. Cl. ...................................... 424/85; 424/59; 424/63; 530/387
[58] Field of Search ................ 424/69.63, 85; 530/387

[56] References Cited

U.S. PATENT DOCUMENTS

| 3,664,994 | 5/1972 | Perper | 424/85 X |
| 4,160,825 | 7/1979 | Sikes | 424/85 |
| 4,645,748 | 2/1987 | Hurwitz et al. | 530/380 |
| 4,732,752 | 3/1988 | Stephan | 424/85 |

*Primary Examiner*—Howard E. Schain
*Attorney, Agent, or Firm*—Fleit, Jacobson, Cohn & Price

[57] ABSTRACT

A composition and method for treating skin which comprises applying an effective amount of polyvalent equine immune whole serum or IgG fraction, in a cosmetically acceptable carrier, to the skin. The polyvalent equine immune whole serum is obtained from horses which have been immunized with a solution containing pig tissue and the IgG fraction is isolated by known chromatographic techniques.

20 Claims, No Drawings

SKIN CARE COMPOSITIONS CONTAINING POLYVALENT EQUINE IMMUNE SERUM

This case is related to U.S. patent application Ser. No. 922,386, now U.S. Pat. No. 4,732,752 entitled "Composition and Method For Treating Rheumatoid Arthritis," which was filed Oct. 23, 1986 and is presently being examined in Group Art Unit 153 by Examiner H. Schain; to U.S. patent application Ser. No. 40,674, entitled "Composition And Method For Treating Acquired Immune Deficiency Syndrome (AIDS)," which was filed Apr. 21, 1987; and, to the U.S. patent application Ser. No. 97,702, entitled "Composition And Method For Treating Arthritis And Related Diseases," which was filed Sept. 17, 1987.

BACKGROUND OF THE INVENTION

1. Field of the Invention

The present invention relates to skin care compositions which contain an effective amount of polyvalent equine immune whole serum or polyvalent equine immune serum IgG fraction.

2. Brief Description of Prior Art

The skin is the largest single organ in the body. It contains millions of cells which, like all other cells in the body, are constantly dying and being replaced. As a person ages, the quality of cells produced deteriorates. The symptoms of aging skin are well-known: wrinkling, crow's feet around the eyes, dry flakiness, crepeyness and sagging.

Good circulation is a prerequisite for healthy skin. In addition, the muscle and connective tissue beneath the skin surface must be healthy and vital if the skin is to maintain a youthful appearance and texture. In view of these requirements, there is a need for skin care compositions which can penetrate the skin and stimulate the skin and underlying connective tissue, blood vessels and muscle.

SUMMARY OF INVENTION

Thus, it is an object of the present invention to provide novel compositions which treat the problems associated with aging skin. It is a further object of the present invention to provide novel compositions which regenerate and rejuvenate the skin.

The present invention provides novel compositions for the care of human skin, which comprise a polyvalent equine immune whole serum or IgG fraction containing antibodies to pig tissue, in cosmetically acceptable carriers.

Generally, the compositions of the present invention contain from 0.01 to 38% by weight of polyvalent equine immune whole serum or fraction as the active ingredient.

In addition to the whole serum or serum fraction, the compositions of the present invention may contain ingredients conventionally used in skin care products, including antioxidants, preservatives, emollients, emulsifiers, vitamins, healing agents, humectants, biological substances, fragrances and perfumes, gelling agents, colorants, anti-irritants, ultra-violet radiation absorbers, sequestering agents, viscosity builders, solubilizers and thickeners.

DETAILED DESCRIPTION OF INVENTION

Generally, the compositions of the present invention contain from about 0.01 to about 0.38% by weight of polyvalent equine immune whole seru or IgG fraction as the active ingredient.

The polyvalent equine immune serum utilized in the compositions of the present invention is prepared by injecting a horse with a suspension of the macerated organs and tissues taken from adult pigs or pigs removed from the mother immediately preceding or at the moment of birth. It is possible to use any and all organs and tissues of the pigs in preparing the antigens for injection into a horse. However, in a preferred embodiment, skin, connective tissue, blood vessels and muscle are utilized.

The organs and tissues are separately homogenized in four times their weight of hydroxyquinoline sulfate solution, utilizing procedures which are well-known in the art. After filtering, 90 ml. each of skin, blood vessel, connective tissue, and muscle homogenate solution are combined to form a concentrated antigen solution. This solution is then divided into 30 ml. aliquots and stored according to procedures well-known in the art. The antigen solution for injection into the horse is prepared by diluting 15 ml. of the concentrated antigen solution with 185 ml. of sterile saline.

To prepare the whole serum of the present invention, 200 ml. of antigen solution is injected into a horse. Injections are repeated at one week intervals, with 5 ml. of concentrated antigen solution being added to the injected material each time until an antibody titer of at least 100 is observed.

Once the required level of antibody production is observed, blood is drawn from the horse and processed to obtain serum, utilizing procedures well-known in the art. The serum is then lyophilized utilizing procedures well-known in the art. To obtain the whole serum of the present invention, the lyophilized serum is reconstituted with sterile, distilled water and the volume adjusted to obtain a protein concentration of 40–60 mg./ml.

The polyvalent equine immune serum thus obtained may be utilized in the compositions of the present invention or may be further fractionated to obtain an IgG fraction for use in the compositions of the present invention. The following procedure is utilized to obtain this IgG fraction:

To reconstitute the lyophilized serum for purposes of obtaining the IgG fraction, 29.52 grams of lyophilized serum is added to 400 ml. of 0.015M $KPO_4$ buffer, pH 8.0 (Buffer A), and stirred for four hours. The serum is dialyzed against four changes of four liters of Buffer A until the conductivity and pH of the sample are the same as that of Buffer A, that is, conductivity =3.33 mS and pH=8.0. Eighty milliliters of the dialyzed serum is removed and held at 4° C. while the rest is fractionated over a 5×40 cm column containing 450 ml. of DEAE Sephadex equilibrated with Buffer A. Nonbound material is collected to obtain a fraction which is then concentrated to 80 milliliters with an Amicon ultrafiltration cell fitted with a YM10 membrane and dialyzed against four changes of four litters of potassium phosphate buffer. The fraction is collected and filtered utilizing methods well known in the art to obtain the fraction utilized in the compositions of the present invention. The amount of protein is determined and the volume adjusted such that 40–60 mg/ml of protein is present in the fraction utilized in the present invention.

Alternatively, the IgG fraction may be obtained directly from polyvalent equine immune whole serum that has not been lyophilized, utilizing procedures known to those skilled in the art.

In addition to the whole serum or serum fraction, the compositions of the present invention may contain ingredients conventionally used in skin care products, including:

antioxidants, such as butylated hydroxyanisole (BHA), preferably in an amount of about 0.02 to 0.05% by weight of the total composition;

preservatives, such as ADUVEX 24, ADUVEX 112, propyl p-hydroxybenzoate, methyl p-hydroxybenzoate, GERMALL 115, bronopol, preferably in a combined amount of about 0.30 to 0.70% by weight of the total composition;

emollients, such as silicone, caprylic or capric acid triglycerides (MIGLYOL 812), carnation white oil (PUREMOR 210), JAGUAR HP-8, squalane, wheat germ oil, avocado oil, and PROCETYL, preferably in a combined amount of about 3.00 to 7.00% by weight;

emulsifiers, such as SPAN 40, TWEEN 40, beeswax, stearic acid (PRISTERENE 4968), glyceral monostearate (GRINDTEK MSP-4P), triethanolamine, LAUREX CS, ARLACEL 165, octyl stearate (CETIOL 868), preferably in a combined amount of about 0.55 to 26% by weight of the total composition;

vitamins, such as DL-alpha tocopherol (vitamin E), preferably in an amount of about 1.00% by weight of the total composition;

healing agents, such as allantoin, preferably in an amount of about 0.20 to 0.30% by weight of the total composition;

humectants, such as sorbitol, glycerine, propylene glycol, and GLUCAM E-20, preferably in a combined amount of about 2.00 to 6.20% by weight of the total composition;

biological substances, such as hydrolastin (HYDROLASTAN), preferably in an amount of about 2.50 to 5.00% by weight of the total composition;

fragrances and perfumes, preferably in an amount of about 0.40 to 0.50% by weight of the total composition;

gelling agents, such as CARBOPOL 940 and triethanolamine, preferably in a combined amount of about 0.30 to 2.60% by weight of the total composition;

colorants, such as FD & C Red and FD & C Yellow, preferably in a combined amount of about 1.00% by weight of the total solution;

anti-irritants, such as alpha-bisabolol and chamomile oil, preferably in an amount of about 0.04 to 0.05% by weight of the total composition;

ultra-violet radiation absorbers, such as PARSOL MCX, preferably in an amount of about 0.80 to 1.60% by weight of the total composition;

sequestering agents, such as disodium EDTA, preferably in an amount of about 0.06% by weight of the total composition;

viscosity builders, such as KELTROL, preferably in an amount of about 0.45% by weight of the total composition;

solubilizers, such as TAGAT L2, preferably in an amount of about 0.20% by weight of the total composition;

and thickeners, such as CARBOPOL 941, preferably in an amount of about 0.045% by weight of the total composition.

To facilitate understanding the advantages and properties of the present invention, the following examples are provided to specifically illustrate the use of the polyvalent equine immune whole serum and IgG fraction in skin care compositions.

EXAMPLE 1—

YOUTH GEL

| PARTS BY WEIGHT | INGREDIENT | SUPPLIER |
|---|---|---|
| 50.00 | Deionized water | |
| 0.02 | ADUVEX 112 Acid | Ward Blenkinsop |
| 0.05 | Bronopol | Boots Co. |
| 1.00 | CARBOPOL 940 | B. F. Goodrich |
| 0.20 | Methyl p-hydroxybenzoate | |
| 2.00 | Glycerin B.P. | |
| 2.00 | Propylene Glycol | |
| 20.00 | Deionized water | |
| 0.05 | Bronopol | |
| 1.60 | Triethanolamine 50% soln. | Shell |
| 5.00 | HYDROLASTAN | S. Black |
| 0.625 | Polyvalent Equine Immune Whole Serum or IgG Fraction | |
| 0.05 | FD & C Red #4, 0.1% soln. | |
| 0.05 | FD & C Yellow #5, 0.1% soln. | |
| 17.355 | Deionized water | |
| 100.00 | | |

Method of Manufacture

1. CARBOPOL 940 SOLUTION: Dissolve the ADUVEX and bronopol in the water and disperse the CARBOPOL with high shear mixing to a smooth solution. Allow to stand for several hours for solution to be completed. Remix to break down any remaining lumps.

2. Warm the glycerine, propylene glycol and methyl p-hydroxybenzoate together until dissolved. Disssolve the bronopol in the second lot of water, warm the solution and add the glycerine/PG/methyl paraben solution with stirring to dissolve. Warm further if necessary to complete solution.

3. Add solution (2) to the CARBOPOL solution with low shear stirring, avoiding aeration.

4. Add the triethanolamine solution with low shear stirring to form the basic gel.

5. Mix the last five ingredients together and then add to the pre-formed gel; blend with low shear mixing.

6. Check the pH value which should be between 5.5 and 6.0. Adjust with 10% triethanolamine if necessary.

The resulting GEL is designed to eliminate blemishes and reduce premature wrinkles. Most effective results may be expected if the GEL is applied two to three times per week, in mornings, after cleansing but before moisturizing. The GEL is allowed to dry and then rinsed off with warm water. The GEL should remain on the skin for at least ten minutes before being removed.

EXAMPLE 2—

CONCENTRATE

| PARTS BY WEIGHT | INGREDIENT | SUPPLIER |
|---|---|---|
| 0.03 | Propyl p-hydroxybenzoate | |
| 0.18 | Methyl p-hydroxybenzoate | |
| 1.18 | Propylene glycol | |
| 72.77 | Deionized water | |
| 0.45 | KELTROL | Kelco A.I.L. Ltd. |
| 4.429 | Deionized water | |
| 0.001 | ADUVEX 112 acid | Ward Blenkinsop |

| PARTS BY WEIGHT | INGREDIENT | SUPPLIER |
|---|---|---|
| 0.025 | Bronopol | Boots Co. |
| 0.045 | CARBOPOL 941 | B. F. Goodrich |
| 2.00 | Silicone Fluid DC-193 | A & E Connock |
| 2.20 | POLYGLYCOL 4000 | Hoechst |
| 2.40 | PROCETYL AWS | Croda Chemicals |
| 5.00 | GLUCAM E-20 | D.F. Anstead |
| 0.04 | Chamomile Oil Roman | Esperis/Jensen Chemical |
| 0.20 | TAGAT L2 | TH Goldschmidt |
| 0.30 | GERMALL 115 or BIOPURE 100 | Blagden-Campbell or Nipa Labs. |
| 0.55 | Triethanolamine 10% solution | |
| 5.00 | HYDROLASTAN | S. Black |
| 3.20 | Polyvalent Equine Immune Whole Serum or IgG Fraction | |
| 100.00 | | |

Method of Manufacture

The use of a mixing vessel incorporating both high and low shear mixers with minimal tendency to aeration is recommended.

1. Dissolve the methyl and propyl p-hydroxybenzoatea in the propylene glycol by warming. Place the water in the main mixing vessel and heat to 70°-80° C.; during this time, the above solution may be added with stirring to dissolve.

2. When up to temperature, sprinkle in the KELTROL with continuous stirring and disperse with high shear until smooth. Continue low shear mixing and hold the temperature for about 30 minutes.

3. Mix the silicone, POLYGLYCOL, PROCETYL and GLUCAM and warm together to give a clear product. Add to the bulk (2) and stir in. Then allow to stand and cool (covered) when any air bubbles will rise to the surface. Make up any lost water.

4. CARBOPOL 941 SOLUTION: Dissolve the ADUVEX and bronopol in the water and disperse the CARBOPOL with high shear. Allow to stand to deaearate.

5. Mix the chamomile oil and TAGAT L2 well and add to bulk (3).

6. Add the GERMALL 115/BIOPURE 100 and stir with low shear to dissolve.

7. Carefully add the CARBOPOL 941 solution, avoiding aeration and blend with low shear mixing.

8. Carefully add the triethanolamine solution and blend in. Allow to stablize for one hour.

9. With the temperature no higher than 30 ° C., add the HYDROLASTAN and the polyvalent equine immune whole serum or IgG fraction of the present invention and blend in carefully.

10. Check the pH value which should be between 6.4 and 6.8. Adjust if necessary with 10% solutions of triethanolamine or citric acid.

The resulting CONCENTRATE can be used on any part of the body to "pick-up" tired skin, but is particularly effective when applied to the face daily for a two week period. After the first two weeks, the CONCENTRATE should be applied on each third day and should also be applied before retiring at night.

| PARTS BY WEIGHT | INGREDIENT | SUPPLIER |
|---|---|---|
| 0.05 | ADUVEX 24 | Ward Blenkinsop |
| 0.05 | BHA | |
| 0.05 | Propyl p-hydroxybenzoate | |
| 0.05 | alpha-BISABOLOL rac. | BASF |
| 0.10 | Silicone Fluid DC.200/100 cs. | A & E Connock |
| 0.80 | PARSOL MCX | Givaudan |
| 1.00 | DL-alpha tocopherol acetate | Roche Products |
| 1.50 | Beeswax white | |
| 3.00 | Squalane natural | A & E Connock |
| 3.00 | LAUREX CS | Albright & Wilson |
| 5.00 | ARLACEL 165 | ICI Specialty Chemicals |
| 73.59 | Deionized water | |
| 0.05 | Sodium tetraborate/BORAX | |
| 0.06 | Disodium EDTA | |
| 0.30 | Allantoin BP | |
| 0.25 | Methyl p-hydroxybenzoate | |
| 5.00 | Glycerine BP | |
| 0.30 | GERMALL 115 or BIOPURE 100 | |
| 5.00 | HYDROLASTAN | S. Black |
| 0.05 | Floral Fragrance C.3753 | Contemporary Perfumers Ltd. |
| 0.80 | Polyvalent Equine Immune Whole Serum or IgG Fraction | |
| 100.00 | | |

Method of Manufacture

1. Heat the first group of eleven ingredients (oil phase) to about 68° C. Mix well.

2. Place the water in the main mixing vessel and heat to 65°-70 ° C. Add the next group of five ingredients (water phase) during the heating.

3. With both up to temperature, add the oil phase to the water phase with high shear mixing to form a fluid emulsion. Continue stirring until homogenous.

4. Cool with stirring adding the GERMALL 115/BIOPURE 100 and the HYDROLASTAN when the temperature has dropped below 60° C.

5. Continue stirring and cooling adding the perfume at about 40° C.

6. When the temperature has dropped below 30° C., add the polyvalent equine immune whole serum or IgG fraction of the present invention and stir/cool to about 25° C. Allow to stand 24 hours.

The resulting LIGHT MOISTURIZER is designed to revitalize the skin and may be used at any time of the day. It is particularly effective when applied to the face after cleansing/toning, as a base for make-up. It may also be applied in the evening.

| PARTS BY WEIGHT | INGREDIENT | SUPPLIER |
|---|---|---|
| 0.05 | alpha-BISABOLOL rac. | BASF |
| 0.05 | Propyl p-hydroxybenzoate | |
| 0.05 | BHA | |
| 0.10 | ADUVEX 24 | Ward Blenkinsop |
| 1.00 | DL-alpha-tocopherol acetate | Roche |
| 1.00 | Wheat germ oil | |
| 1.00 | LAUREX CS | Albright & Wilson |
| 1.60 | PARSOL MCX | Givaudan |
| 2.00 | Avocado oil | |
| 3.00 | Stearic Acid/PRISTERENE 4968 | Unichema |
| 5.00 | MIGLYOL 812 | Dynamit-Nobel |
| 6.00 | ARLACEL 165 | ICI Specialties |
| 15.00 | CETIOL 868 | Henkel |
| 0.25 | Methyl p-hydroxybenzoate | |
| 0.30 | Allantoin | |
| 0.60 | Triethanolamine | |
| 4.00 | Propylene glycol | |
| 52.65 | Deionized water | |
| 0.30 | BIOPURE 100 | Nipa Labs. |
| 0.05 | Perfume C.3753 | Contemporary Perfumers |
| 5.00 | HYDROLASTAN | S. Black |
| 1.00 | Polyvalent Equine Immune Whole Serum or IgG Fraction | |
| 100.00 | | |

Method of Manufacture

1. Heat the first group of thirteen materials (oil phase) to about 68° C. Mix well.

2. Place the water in the main mixing vessel and heat to 65°-70° C. Add the next group of four ingredients (water phase) during the heating.

3. With both phases up to temperature, add the oil phase to the water phase with high shear mixing to form a fluid emulsion. Continue stirring until homogeneous.

4. Cool with stirring, adding the BIOPURE 100 and the HYDROLASTAN when the temperature has dropped below 60° C.

5. Add the perfume at about 50° C. and transfer to low shear mixing when the cream is thickening up. Continue cooling.

6. When the temperature has dropped to 30° C. or below, add the polyvalent equine immune whole serum or IgG fraction of the present invention and stir/cool to about 25° C. Allow to stand 24 hours.

The resulting CONCENTRATED MOISTURIZER is designed for older or more dehydrated skins than would be expected to benefit from the LIGHT MOISTURIZER of Example 2 and is applied in the same way.

EXAMPLE 5—
HAND & BODY LOTION

| PARTS BY WEIGHT | INGREDIENT | SUPPLIER |
|---|---|---|
| 0.02 | BHA | |
| 0.05 | ADUVEX 24 | Ward Blenkinsop |
| 0.05 | Propyl p-hydroxybenzoate | |
| 0.20 | Silicone Fluid DC.200/100 cS | A & E Connock |
| 0.80 | SPAN 40 | ICI Specialty Gr. |
| 0.80 | TWEEN 40 | ICI Specialty Gr. |
| 0.90 | Beeswax white | |
| 0.90 | PRISTERENE 4968 | Unichema |
| 1.00 | DL-alpha-tocopherol acetate | Roche Products |
| 2.40 | MIGLYOL 812 | Dynamit Nobel |
| 2.40 | GRINDTEX MSP-40 | Grindsted Prod. |
| 3.30 | PUREMOR 210 | Burmah |
| 58.03 | Deionized water | |
| 0.20 | Methyl p-hydroxybenzoate | |
| 0.20 | Allantoin BP | |
| 0.30 | Triethanolamine 50% soln. | |
| 2.00 | Sorbitol soln. 70% | |
| 3.00 | Glycerine BP | |
| 0.20 | JAGUAR HP-8 | Chesam Chemicals |
| 20.00 | Deionized water | |
| 0.30 | GERMALL 115 or or BIOPURE 100 | Blagden Campbell or Nipa Labs. |
| 2.50 | HYDROLASTAN | S. Black |
| 0.05 | Floral Fragrance C.3753 | Contemporary Perfumers |
| 0.40 | Polyvalent Equine Immune Whole Serum or IgG Fraction | |
| 100.00 | | |

Method of Manufacture

1. Heat the first group of twelve ingredients (oil phase) to about 68° C. Mix well.

2. Heat the first lot of water in the main mixing vessel to about 70° C. and add the following group of five ingredients (water phase).

3. With both phases up to temperature, add the oil phase to the water phase with high shear mixing to form a smooth fluid emulsion. Mix until homogeneous.

4. Stir the JAGUAR HP-8 into the next lot of water until fully wetted and dissolved. Allow to stand cold to fully dissolve.

5. Add the JAGUAR solution to the emulsion and mix with high shear to disperse. Switch to low shear to blend. Alternatively, the JAGUAR powder could be gradually sprinkled directly into the pre-formed emulsion, dispersed and then the rest of the water added cold.

6. Cool with stirring, adding the GERMALL 115/BIOPURE 100 and the HYDROLASTAN when the temperature has dropped below 60° C.

7. When the temperature has dropped to 40° C., add the perfume.

8. When the temperature has dropped to 30° C., add the polyvalent equine immune whole serum or IgG fraction of the present invention and stir to uniformity.

The resulting HAND & BODY LOTION is designed to improve the tone and texture of the skin. The LOTION can be applied, at any time, to the hands and is particularly effective when applied after exposure to water or other irritants. The LOTION is also particularly effective when applied to the body after bathing or exposure to sun. The LOTION may be applied more generously to areas with dry skin, sagging tissue, or poor muscle tone.

What is claimed is:

1. A skin care composition comprising an amount from about 0.01 to about 38% by weight relative to the total weight of the composition of polyvalent equine immune whole serum or IgG fraction containing antibodies to pig skin, connective tissue, blood vessels and muscle.

2. A skin care composition according to claim 1 which additionally comprises at least one antioxidant, in an amount from about 0.02 to about 0.05% by weight of the total composition.

3. A skin care composition according to claim 1 which additionally comprises at least one preservative, in an amount from about 0.30 to about 0.70% by weight of the total composition.

4. A skin care composition according to claim 1 which additionally comprises at least one emollient, in an amount from about 3.00 to about 7.00% by weight of the total composition.

5. A skin care composition according to claim 1 which additionally comprises at least one emulsifier, in an amount from about 0.55 to about 26% by weight of the total composition.

6. A skin care composition according to claim 1 which additionally comprises at least one vitamin, in amount of about 1.00% by weight of the total composition.

7. A skin care composition according to claim 1 which additionally comprises at least one healing agent, in an amount from about 0.20 to about 0.30% by weight of the total composition.

8. A skin care composition according to claim 1 which additionally comprises at least one humectant, in an amount from about 2.00 to about 6.20% by weight of the total composition.

9. A skin care composition according to claim 1 which additionally comprises at least one biological substance, in an amount from about 2.50 to about 5.00% by weight of the total composition.

10. A skin care composition according to claim 1 which additionally comprises at least one perfume, in an amount from about 0.40 to about 0.50% by weight of the total composition.

11. A skin care composition according to claim 1 which additionally comprises at least one gelling agent, in an amount from about 0.30 to about 2.60% by weight of the total composition.

12. A skin care composition according to claim 1 which additionally comprises at least one colorant, in an amount of about 1.00% by weight of the total composition.

13. A skin care composition according to claim 1 which additionally comprises at least one anti-irritant, in an amount from about 0.04 to about 0.05% by weight of the total composition.

14. A skin care composition according to claim 1 which additionally comprises at least one ultra-violet radiation absorber, in an amount from about 0.80 to about 1.60% by weight of the total composition.

15. A skin care composition according to claim 1 which additionally comprises at least one sequestering agent, in an amount of about 0.06% by weight of the total composition.

16. A skin care composition according to claim 1 which additionally comprises at least one viscosity builder, in an amount of about 0.45% by weight of the total composition.

17. A skin care composition according to claim 1 which additionally comprises at least one solubilizer, in an amount of about 0.20% by weight of the total composition.

18. A skin care composition according to claim 1 which additionally comprises at least one thickener, in an amount of about 0.045% by weight of the total composition.

19. A skin care composition according to claim 1 which is in the form of a gel, concentrate, cream, or lotion.

20. A method of treating skin which comprises applying to the skin an effective amount of a composition having as the essential active ingredient polyvalent equine immune whole serum or IgG fraction containing antibodies to pig skin, connective tissue, blood vessels and muscle.

* * * * *